(12) United States Patent
Heath et al.

(10) Patent No.: US 8,097,574 B2
(45) Date of Patent: Jan. 17, 2012

(54) PERSONAL CLEANSING COMPOSITIONS COMPRISING A BACTERIAL CELLULOSE NETWORK AND CATIONIC POLYMER

(75) Inventors: Benjamin Parker Heath, Cincinnati, OH (US); Timothy Woodrow Coffindaffer, Maineville, OH (US); Kenneth Eugene Kyte, III, Oregonia, OH (US); Edward Dewey Smith, III, Mason, OH (US); Shawn D. McConaughy, Cincinnati, OH (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 12/854,340

(22) Filed: Aug. 11, 2010

(65) Prior Publication Data

US 2011/0039744 A1 Feb. 17, 2011

Related U.S. Application Data

(60) Provisional application No. 61/233,976, filed on Aug. 14, 2009.

(51) Int. Cl.
*C11D 3/48* (2006.01)
*C11D 1/02* (2006.01)

(52) U.S. Cl. ........ 510/137; 510/119; 510/130; 510/139; 510/151; 510/426; 510/427

(58) Field of Classification Search .................. 510/119, 510/130, 137, 139, 151, 426, 427
See application file for complete search history.

(56) References Cited

U.S. PATENT DOCUMENTS

| | | | |
|---|---|---|---|
| 6,241,812 B1 * | 6/2001 | Smith et al. ................ | 106/162.9 |
| 2008/0146485 A1 * | 6/2008 | Swazey ......................... | 510/446 |
| 2010/0009891 A1 * | 1/2010 | Canto et al. ..................... | 510/418 |
| 2010/0197553 A1 * | 8/2010 | Barnabas et al. ............. | 510/236 |
| 2010/0210501 A1 * | 8/2010 | Caggioni et al. .............. | 510/338 |
| 2010/0240569 A1 * | 9/2010 | Boutique et al. .............. | 510/299 |
| 2010/0240571 A1 * | 9/2010 | Boutique et al. .............. | 510/338 |
| 2010/0322878 A1 * | 12/2010 | Stella et al. ..................... | 424/59 |

* cited by examiner

*Primary Examiner* — Charles Boyer
(74) *Attorney, Agent, or Firm* — Jay A. Krebs; Ronald Terk Sia

(57) ABSTRACT

A personal cleansing composition comprising a liquid matrix comprising water; a lathering surfactant; and an external structurant comprising a bacterial cellulose network and a cationic polymer; wherein a particulate material is suspended within the liquid matrix and the composition has a compositional pH of less than about 7. Methods of use and making are also provided.

14 Claims, No Drawings

PERSONAL CLEANSING COMPOSITIONS COMPRISING A BACTERIAL CELLULOSE NETWORK AND CATIONIC POLYMER

CROSS REFERENCE TO RELATED APPLICATION

This application claims the benefit of U.S. Provisional Application No. 61/233,976 filed on Aug. 14, 2009.

BACKGROUND OF THE INVENTION

Personal cleansing compositions including facial cleansers, while good at removing sebum and grime from the skin and hair, may cause skin irritation and, or damage to the surfaces being cleansed. Personal cleansing compositions are typically detersive in nature, meaning that they performing a cleaning function, and often have an acidic pH (below 7). Further, formulations containing lower amounts of active ingredients (such as detersive surfactants) with sufficient cleansing and conditioning benefits can be desirable. The addition of suspended particles and, or droplets of materials such as oils or petrolatum has been attempted in order to provide cleansing and conditioning benefits. See U.S. Patent Publ. No. 2005/0201965.

Releveling of active ingredients has made suspension particles an attractive technology to maintain performance benefits but the reduction of actives results in changes to the rheology of the compositions as many active ingredients provide some degree of rheology modification (such as shear thickening and particle suspension capabilities). Ingredients which provide a functional benefit, such as cleaning or conditioning, and impact rheology are referred to as "internal structurants."

Attempts to introduce structuring agents into various detersive compositions have been described. Known external structuring agents include polymers or gums, many of which are known to swell or expand when hydrated to form random dispersion of independent microgel particles. Examples of polymers and gums include: gellan gum, pectine, alginate, arabinogalactan, caageenan, xanthum gum, guar gum, rhamsan gum, furcellaran gum, carboxymethylcellulose and cellulose. See e.g. U.S. Pat. No. 6,258,771 to Hsu et al. U.S. Pat. No. 6,077,816 to Puvvada et al.; and WO 2006/116099 to Fleckenstein et al. These polymer or gum structurants are typically needed at relatively high levels which have been found to leave certain compositions opaque and cloudy in appearance. Further, certain suspension polymers, such as acrylate cross-linked acid copolymers such as disclosed in"Polymer For Personal Care, Carbopol EDT® Resins: Formulation Tips", March 1994 by Noveon™, Inc. have been described (disclosing the use of polyol, such as glycerin or polyethylene glycol). Many of these suspension polymers, however, have been found by consumers to feel slimy and/or do not rinse easily off after use. This is particularly undesirable for personal cleansing compositions as they are used on the body where consumer hand feel is important.

The addition of certain structurants which are believed to form fibrous networks have been described as providing desirable rheological modification benefits without composition opacity. See U.S. Patent Publ. No. 2008/108714 A1 (disclosing microfibrous cellulose for use in various detergent compositions and U.S. Patent Publ. No. 2005/203213 A1 (disclosing the use of non-polymeric crystalline hydroxyl-functional materials and polymeric structurants such as polyacrylates, polysaccharides, and polymer gums). These and other structuring agents can be referred to as "external structurants" as they are added primarily for rheology modification purposes and not for an active benefit such as cleaning, conditioning, or fragrance.

It has been found, however, that microfibrous celluloses alone fail to provide sufficient rheological benefits for certain personal care compositions, such as those with low levels of internal structurants and/or acidic pH, or where high levels of or very large/dense particulates are desired, such as in scrubs or facial cleansers. Further, there is a need for structuring systems which are less susceptible to the negative side effects observed with some known structuring systems, such as causing compositional opacity and filmy or slimy feel during use.

SUMMARY OF THE INVENTION

One aspect of the present invention provides for a personal cleansing composition comprising a liquid matrix comprising water; a lathering surfactant; and an external structurant comprising both a bacterial cellulose network and a cationic polymer, such as a derivatized quaternized hydroxyethyl cellulose ethers, a cellulose ether, a guar gum, cationic polysaccharide polymers, such as cationic cellulose derivatives and cationic starch derivatives, and mixtures thereof; wherein a particulate material is suspended within the liquid matrix and the composition has a compositional pH of less than about 7, or less than about 4.

Another aspect of the present invention from about 0.05% to about 0.5% of a bacterial cellulose network; from about 0.005% to about 0.5% of a cationic polymer selected from the group consisting of a derivatized quaternized hydroxyethyl cellulose ether, a cellulose ether, a guar gum, a polysaccharide polymers, and a mixture thereof; from about 0.1% to about 30% of a particulate material; from about 4% to about 30% of a lathering surfactant; and a compositional pH of less than about 4.

These compositions provide good lathering and readily rinse off without leaving undesirable levels of slimy or filmy hand feel. The particulate materials enhance cleansing and exfoliation as well as provide conditioning benefits without damage or irritation. Formulations having pH less than about 4 are particularly preferable to enable formulation of salicylic acid formulations with the benefits of suspended dispersed phase materials.

DETAILED DESCRIPTION OF THE INVENTION

The personal cleansing composition of the present invention comprises a liquid matrix comprising an external structuring system comprising a bacterial cellulose network and a cationic polymer. Additional structurants can also be used. In one embodiment, the external structuring system consists essentially of a bacterial cellulose network and a cationic polymer. In one embodiment, the bacterial cellulose network is formed from individual bacterial cellulose fibers which are activated in the presence of water and a cationic polymer. Without intending to be bound by theory, it is believed that the addition of the cationic polymer, as a secondary structuring agent, enhances the structuring benefits of the bacterial cellulose network such that it is capable of suspending larger amounts of particulates or more dense particulates which would settle or float in formulations comprising just the bacterial cellulose network alone. In one embodiment, the weight ratio of bacterial cellulose network to cationic polymer is from about 1.5:1 to about 100:1, or from about 2:1 to about 50:1, or from about 2.5:1 to about 5:1.

1. Bacterial Cellulose Network

The personal cleansing composition of the present invention comprises a bacterial cellulose network at a level of about 0.05 to about 1, preferably from about 0.1 to about 0.8, more preferably from about 0.2 to about 0.5, most preferably about 0.25 percent by weight. The term "bacterial cellulose" is intended to encompass any type of cellulose produced via fermentation of a bacteria of the genus *Acetobacter* and includes materials referred popularly as microfibrillated cellulose, reticulated bacterial cellulose, and the like.

Without intending to be bound by theory, it is believed that the bacterial cellulose network provides desirable rheology modification benefits such as increasing particle suspension capabilities as measured by yield stress while maintaining compositional clarity and avoiding the slimy hand feel encountered with polymer and gum structurants.

The bacterial cellulose network is formed by processing of a mixture of the bacterial cellulose in a hydrophilic solvent, such as water, polyols (e.g., ethylene glycol, glycerin, polyethylene glycol, etc.), or mixtures thereof. This processing is called "activation" and comprises, generally, high pressure homogenization and/or high shear mixing. It has importantly been found that activating the bacterial cellulose under sufficiently intense processing conditions provides for increased yield stress at given levels of bacterial cellulose network. Yield stress, as defined below, is a measure of the force required to initiate flow in a gel-like system. It is to be believed that yield stress is indicative of the suspension ability of the liquid composition, as well as the ability to remain in situ after application to a vertical surface.

Activation is a process in which the 3-dimensional structure of the bacterial cellulose is modified such that the cellulose imparts functionality to the base solvent or solvent mixture in which the activation occurs, or to a composition to which the activated cellulose is added. In one embodiment, the bacterial cellulose network is formed from activating the bacterial cellulose fibers in the presence of water. The cationic polymer can then be added in a later step with other optional ingredients under various levels of stress. In another embodiment, the activation is done with cationic polymer present. Without intending to be bound by theory, it is believed that activating the bacterial cellulose network with cationic polymer allows the resultant network structure to be formed with higher amounts of interconnectivity between the fibers (possibly from the cationic polymer forming additional binding sites between fibers). This increased interconnectivity is believed to help increase the rheology modification benefits which includes, but is not limited to, providing such properties as imparting particle suspension capabilities as measured by yield stress. The activation of the bacterial cellulose expands the cellulose portion to create a bacterial cellulose network, which is a reticulated network of highly intermeshed fibers with a very high surface area. The activated reticulated bacterial cellulose possesses an extremely high surface area that is thought to be at least 200-fold higher than conventional microcrystalline cellulose (i.e., cellulose provided by plant sources).

The bacterial cellulose utilized herein may be of any type associated with the fermentation product of *Acetobacter* genus microorganisms, and was previously available, examples, from CPKelco U.S. include AxCEL CG-PX and CELLULON®. Such aerobic cultured products are characterized by a highly reticulated, branching interconnected network of fibers that are insoluble in water. The preparation of such bacterial cellulose products are well known and typically involve a method for producing reticulated bacterial cellulose aerobically, under agitated culture conditions, using a bacterial strain of *Acetobacter aceti* var. *xylinum*. Use of agitated culture conditions results in sustained production, over an average of 70 hours, of at least 0.1 g/liter per hour of the desired cellulose. Wet cake reticulated cellulose, containing approximately 80-85% water, can be produced using the methods and conditions disclosed in the above-mentioned patents. Dry reticulated bacterial cellulose can be produced using drying techniques, such as spray-drying or freeze-drying, that are well known. See U.S. Pat. Nos. 5,079,162 and 5,144,021.

*Acetobacter* is characteristically a gram-negative, rod shaped bacterium 0.6-0.8 microns by 1.0-4 microns. It is a strictly aerobic organism; that is, metabolism is respiratory, not fermentative. This bacterium is further distinguished by the ability to produce multiple poly β-1,4-glucan chains, chemically identical to cellulose. The microcellulose chains, or microfibers, of reticulated bacterial cellulose are synthesized at the bacterial surface, at sites external to the cell membrane. These microfibers have a cross sectional dimensions of about 1.6 nm to about 3.2 nm by about 5.8 nm to about 133 nm. In one embodiment, the bacterial cellulose network has a widest cross sectional microfiber width of from about 1.6 nm to about 200 nm, alternatively less than about 133 nm, alternatively less than about 100 nm, alternatively less than about 5.8 nm. Additionally, the bacterial cellulose network has an average microfiber length of at least 100 nm, alternatively from about 100 to about 1500 nm. In one embodiment, the bacterial cellulose network has a microfiber aspect ratio, meaning the average microfiber length divided by the widest cross sectional microfiber width, of from about 10:1 to about 1000:1, or from about 100:1 to about 400:1, or from about 200:1 to about 300:1.

The presence of the bacterial cellulose network can be detected by a STEM micrograph imaging. A sample is obtained. A 1500 mesh copper TEM grid is placed on filter paper and 15 drops of the sample are applied to the TEM grid. The TEM grid is transferred to fresh filter paper and rinsed with 15 drops of deionized water. The TEM grid is then imaged in a S-5200 STEM micrograph instrument to observe for a fibrous network. Those of skill in the art will understand that if a fibrous network is detected, the cross dimensional of the fibers as well as the aspect ratio can be determined. Those of skill in the art will also recognized that alternative analytic techniques can be used to detect the presence of the bacterial cellulose network such as Atomic Force Microscopy using the same TEM grid and deposition and rinsing steps as disclosed above. An Atomic Force Microscopy 3D representation can be obtained showing the fiber dimensions as well as degree of networking.

The small cross sectional size of these *Acetobacter*-produced fibers, together with the large length and the inherent hydrophilicity of cellulose, provides a cellulose product having an unusually high capacity for absorbing aqueous solutions. Additives have often been used in combination with the bacterial cellulose to aid in the formation of stable, viscous dispersions. Non-limiting examples of additional suitable bacterial celluloses are disclosed in and U.S. Pat. Nos. 6,967,027 to Heux et al.; 5,207,826 to Westland et al.; 4,487,634 to Turbak et al.; 4,373,702 to Turbak et al. and 4,863,565 to Johnson et al., U.S. Pat. Publ. No. 2007/0027108 to Yang et al.

In one embodiment, the external structuring system further comprises a bacterial cellulose which is at least partially coated with a polymeric thickener. This at least partially coated bacterial cellulose can be prepared in accordance with the methods disclosed in U.S. Pat. Publ. No. 2007/0027108 to Yang et al. at ¶¶8-19. In one suitable process, the bacterial cellulose is subjected to mixing with a polymeric thickener to at least partially coat the bacterial cellulose fibers and bundles. It is believed that the commingling of the bacterial cellulose and the polymeric thickener allows for the desired generation of a polymeric thickener coating on at least a portion of the bacterial cellulose fibers and/or bundles.

In one embodiment the method of producing said at least partially coated bacterial cellulose comprises a proportion of bacterial cellulose to polymeric thickener comprises from about 0.1% to about 5% of the bacterial cellulose, alternatively from about 0.5% to about 3.0%, by weight of the added polymeric thickener; and from about 10% to about 900% of the polymeric thickener by weight of the bacterial cellulose.

In one embodiment the polymeric thickener comprises a hydrocolloid, at least one charged cellulose ether, at least one polymeric gum, and mixtures thereof. One suitable hydrocolloid includes carboxymethylcellulose ("CMC"). Suitable polymeric gums comprises xanthan products, pectin, alginates, gellan gum, welan gum, diutan gum, rhamsan gum, kargeenan, guar gum, agar, gum Arabic, gum ghatti, karay gum, gum tragacanth, tamarind gum, locust bean gum, and the like and mixtures there.: See U.S. Pat. Publ. No. 2007/0027108 at ¶¶6 and 16.

In another embodiment, the bacterial cellulose undergoes no further modified either chemically or physically aside from the activation and/or the polymeric thickener coating. In one embodiment, the bacterial cellulose is free of a chemical modification comprising esterification or etherification by the addition of hydrophobic groups onto the fibers, meaning that the bacterial cellulose fibers are not modified to be surface active, wherein surface active means the ingredient lowers the surface tension of the medium in which it is dissolved. In another embodiment, the bacterial cellulose is free of any physical modification including coating the fibers with hydrophobic materials. In one embodiment, the fibers are not modified as described in WO 2007/068344.

2. Cationic Polymer

The personal cleansing composition of the present invention comprises a cationic polymer as a secondary structurant to be used in addition to the bacterial cellulose network. The cationic polymer is used at a level of about 0.005 to about 1, or from about 0.01 to about 0.8, or from about 0.05 to about 0.5, or from about 0.1 to about 0.2 percent by weight. Nonlimiting examples of suitable cationic polymers comprise a derivatized quaternized hydroxyethyl cellulose ethers, a hydrophobically modified quaternized hydroxyethyl cellulose ether cationic polysaccharide polymers, such as cationic cellulose derivatives, cationic guars and cationic starch derivatives, and mixtures thereof.

Nonlimiting examples of derivatized quaternized hydroxyethyl cellulose ethers include: those referred to in the industry by Personal Care Products Council (formerly the Cosmetic, Toiletry, and Fragrance Association) as polyquaternium-10 from Amerchol which are described in U.S. Pat. No. 3,472,840A from Union Carbide and U.S. Pat. No. 3,962,418A from Procter & Gamble; and polyquaternium-67 from Amerchol which is described in WO 2008 042635 from Union Carbide and US 2007 0031362 A1 from Union Carbide, and can be referred to by those skilled in the art as SoftCAT.

"Quaternized cellulose ethers" refers to cellulose ether derivatives containing quaternary ammonium groups. Generally, the cellulose ether component comprises anhydroglucose repeat units derivatized with certain ethers. For example, the term "M.S. (hydroxyethyl)" designates the average number of moles of hydroxyethyl groups which have been attached by an ether linkage per mole of anhydroglucose unit.

In one embodiment, cellulose ethers used to make quaternized cellulose ethers of the present invention have an M.S. (hydroxyethyl) of from 1.0 to 3.5, or from 1.5 to 2.5, or from 1.8 to about 2.4, or from about 2.0 to about 2.2. In one embodiment, the quaternized cellulose ethers of the present invention have a nitrogen percentage (% N—average weight percent of nitrogen per anhydroglucose repeat unit) from about 0.3 to about 3.0. In such an embodiment, the cellulose ethers used to make quaternized cellulose ethers can generally have at least 250 anhydroglucose repeat units, preferably at least 350 anhydroglucose repeat units. In a further embodiment, the cellulose ethers have fewer than 4000 anhydroglucose repeat units, preferably fewer than 3750, preferably fewer than 3500, preferably fewer than 3250, preferably fewer than 3000, preferably fewer than 2500 and more preferably fewer than 2000 anhydroglucose repeat units. Such cellulose ethers are readily commercially available. Alternatively, such cellulose ethers can be prepared from cellulose by methods known to those skilled in the art.

Typical cellulose ethers include for example, hydroxyethyl cellulose, hydroxypropyl cellulose, methyl cellulose, hydroxypropyl methyl cellulose, hydroxyethyl methyl cellulose or hydroxyethyl carboxylmethyl cellulose. Preferred cellulose ethers include hydroxyethyl cellulose and hydroxypropyl cellulose. Other suitable cellulose ethers comprise hydroxyethyl groups. The above cellulose ethers can be derivatized with a hydrophobic substituent and a cationic nitrogen-containing substituent to form quaternized cellulose ethers of the present invention.

Suitable cationic polymers for use in the composition include polysaccharide polymers, such as cationic cellulose derivatives and cationic starch derivatives. Suitable cationic polysaccharide polymers include those which conform to the formula

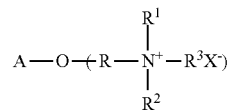

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion. Non limiting examples of such counterions include halides (e.g., chloride, fluoride, bromide, iodide), sulfate, methylsulfate, and combinations thereof.

Preferred quaternized cellulose polymers with hydrophobic substitution are referred to in the industry Personal Care Products Council (formerly the Cosmetic, Toiletry, and Fragrance Association) as Polyquaternium-67 and are available from Dow Chemical (Amerchol Corp.) under the tradename SoftCAT™ which includes their SL, SX, and SK series polymers. Other preferred cationic cellulose polymers are salts of hydroxyethyl cellulose reacted with trimethyl ammonium substituted epoxide, referred to in the industry (CTFA) as Polyquaternium-10 and are available from Dow Chemical (Amerchol Corp.) in their UCare™ Polymer LR, and JR series of polymers.

In one embodiment, the cationic polymer comprises hydrophobically modified quaternized hydroxyethyl cellulose ethers, such as described in US 2007 0031362 A1 from Union Carbide.

"Hydrophobically modified quaternized cellulose ethers" refers to cellulose ether derivatives containing quaternary ammonium groups. In one embodiment, the quaternized cellulose ether comprises a cellulose ether which has from 4,000 to 10,000 anhydroglucose repeat units and which is substituted with (a) on the average from 0.0003 to 0.08 moles, per mole of anhydroglucose unit, of a substituent comprising an alkyl or arylalkyl group having from 8 to 24 carbon atoms and (b) a substituent having the formula II $$[R^5R^6R^7R^8N+](A^{z-})_{1/z} \quad (II)$$

wherein $R^5$, $R^6$ and $R^7$ each independently are —$CH_3$ or —$C_2H_5$, $R^8$ is —$CH_2$—CHOH—$CH_2$— or —$CH_2CH_2$—

$A^{z-}$ is an anion, and z is 1, 2 or 3.

Preferably, these cellulose ethers have an M.S. (hydroxyethyl) of from 1.0 to 3.0, more preferably from 1.5 to 2.5. The M.S. (hydroxyethyl) designates the average number of moles of hydroxyethyl groups which have been attached by an ether linkage per mole of anhydroglucose unit. The cellulose ethers of this embodiment have at least 4,000 anhydroglucose repeat units, preferably at least 4,500 anhydroglucose repeat units, more preferably at least 5,000 anhydroglucose repeat units, and most preferably at least 6,000 anhydroglucose repeat units. The cellulose ethers have up to 10,000 anhydroglucose repeat units, preferably up to 9,000 anhydroglucose repeat units and most preferably up to 8,000 anhydroglucose repeat units. Such cellulose ethers are readily commercially available. Alternatively, such cellulose ethers can be prepared from cellulose by methods known in the art.

Typical cellulose ethers include for example, hydroxyethyl cellulose, hydroxypropyl cellulose, methyl cellulose, hydroxypropyl methyl cellulose, hydroxyethyl methyl cellulose, hydroxyethyl carboxylmethyl cellulose, or mixtures thereof. Preferred cellulose ethers include hydroxyethyl cellulose and hydroxypropyl cellulose. Other suitable cellulose ethers s comprise hydroxyethyl groups. The above cellulose ethers can be derivatized with a hydrophobic substituent and a cationic nitrogen-containing substituent to form quaternized cellulose ethers of the present invention.

The cellulose ether derivatives of the present invention are cellulose ethers which are substituted with a hydrophobic substituent (a) and a cationic substituent (b) as described below. Hydrophobic substituents (a) suitable for use in accordance with the present invention comprise an alkyl or arylalkyl group having from 8 to 24 carbon atoms, preferably from 10 to 24 carbon atoms, more preferably from 12 to 18 carbon atoms, and most preferably 12 to 15 carbon atoms. As used herein the term "arylalkyl group" means a group containing both aromatic and aliphatic structures. The most preferred aliphatic hydrophobic substituent is the dodecyl group, which is most preferably straight-chained. The hydrophobic substituent is typically cationic or non-ionic. Many hydrophobe-containing reagents suitable for use as hydrophobic substituents are commercially available. In addition, methods for preparing such hydrophobe-containing reagents, as well as methods for derivatizing cellulose ethers to comprise such hydrophobic substituents, are known to those skilled in the art. Note for example, U.S. Pat. No. 4,228,277, U.S. Pat. No. 4,663,159, and U.S. Pat. No. 4,845,175.

A preferred hydrophobic substituent (a) suitable for use in accordance with the present invention has the formula (I)

$$R^1R^2R^3R^4N^+(A^{z-})_{1/z} \quad (I)$$

wherein $R^1$ and $R^2$ each independently are —$CH_3$ or —$C_2H_5$, $R^3$ is —$CH_2$—CHOH—$CH_2$— or —$CH_2CH_2$—

$R^4$ is an alkyl or arylalkyl group having from 8 to 24 carbon atoms, and $A^{z-}$ is an anion and z is 1, 2 or 3.

Preferably, $R^1$ and more preferably, both $R^1$ and $R^2$ are —$CH_3$. Preferably, $R^3$ is —$CH_2$—CHOH—$CH_2$—. Preferably, $R^4$ is —$C_nH_{(2n+1)}$, where n is from 8 to 24, more preferably from 10 to 18, most preferably 12. $A^{z-}$ is an anion with the valency of z, such as phosphate, nitrate, sulfate or halide. Chloride is the most preferred ion. Z is preferably 1 or 2, more preferably 1. The most preferred hydrophobic substituents (a) are those wherein two or more, preferably each of $R^1$, $R^2$, $R^3$, $R^4$, $A^{z-}$ and z have the mentioned preferred meanings.

Other preferred hydrophobic substituents include those derived from hydrophobe-containing reagents comprising alkyl or arylalkyl groups having from 8 to 24 carbon atoms, preferably from 10 to 24 carbon atoms, more preferably from 12 to 18 carbon atoms, and most preferably 12 to 15 carbon atoms. Preferred are glycidyl ethers, such, as nonylphenyl glycidyl ether or dodecylphlelnl glycidyl ether; or alpha-olefin epoxides, such as 1,2-epoxy hexadecane and their respective chlorohydrins, or alkyl halides, e.g., dodecyl bromide, and mixtures thereof.

The average substitution level of the substituent (a) is at least 0.0003, preferably at least 0.0005 moles per mole of anhydroglucose unit and up to 0.08, preferably up to 0.07, and most preferably up to 0.05 moles per mole of anhydroglucose unit. More than one particular hydrophobic substituent can be substituted onto the cellulose ether provided that the total substitution level is within the ranges set forth above.

The cationic substituent (b) suitable for use in accordance with the present invention has the formula II (above). Preferably, $R^5$ is —$CH_3$. More preferably, $R^5$, $R^6$ and $R^7$ are —$CH_3$. Preferably, $R^8$ is —$CH_2$—CHOH—$CH_2$—. $A^{z-}$ is an anion with the valency of z, such as phosphate, nitrate, sulfate or halide. Chloride is the most preferred ion. Z is preferably 1 or 2, more preferably 1. The most preferred cationic substituents (b) are those wherein two or more, preferably each of $R^5$, $R^6$, $R^7$, $R^8$, $A^{z-}$ and z have the mentioned preferred meanings.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Nonlimiting examples of suitable cationic guar gum as described in U.S. Patent Publ. No 2008/0187507 at paragraph 101. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

3. Additional Structuring Agents

In one embodiment, the external structuring system further comprises additional structuring agents such as non-polymeric crystalline hydroxyl-functional materials, polymeric structuring agents, and mixtures thereof.

a. Non-Polymeric Crystalline Hydroxyl-Functional Materials

One suitable additional structuring agent comprises a non-polymeric (except for conventional alkyoxlation), crystalline hydroxyl-functional materials, which forms thread-like structuring systems throughout the liquid matrix when they are crystallized within the matrix in situ. Such materials can be generally characterized as crystalline, hydroxyl-containing fatty acids, fatty esters or fatty waxes. See e.g. U.S. Pat. No. 7,169,741 at col. 9, line 61 to col. 11, line 4, and U.S. Pat. No. 6,080,708 and in WO Publ. No. 2002/0040627.

b. Polymeric Structuring Agents

Other types of organic structuring agents, besides the non-polymeric, crystalline, hydroxyl-containing structuring agents described in the previous section, may be utilized in the personal cleansing compositions herein. Polymeric materials which will provide particle suspension capabilities to the liquid matrix may also be employed. Suitable polymeric structuring agents include those of the polyacrylate, polysaccharide or polysaccharide derivative type. Polysaccharide derivatives typically used as structuring agents comprise polymeric gum materials. Such gums include pectine, alginate, arabinogalactan (gum Arabic), carrageenan, gellan gum, xanthan gum and guar gum. Gellan gum is a heteropolysaccharide prepared by fermentation of Pseudomonaselodea ATCC 31461 and is commercially marketed by CP Kelco U.S., Inc. under the KELCOGEL tradename. Processes for preparing gellan gum are described in U.S. Pat. Nos. 4,326,052; 4,326,053; 4,377,636 and 4,385,123.

In one embodiment, the external structuring system is free of or essentially free of any additional structuring agent known in the art such as those listed herein, for example: free of or essentially free of non-polymeric crystalline hydroxyl-functional materials; free or essentially free of polymeric structuring agents including polymeric gums, pectine, alginate, arabinogalactan (gum Arabic), carrageenan, gellan gum, xanthan gum and guar gum. It has importantly been found that the external structuring system of the present invention provides sufficient rheological benefits, such as bead suspension.

4. Particulate Materials

Particulate materials for use in the present invention can generally be generally classified into one of two groups. These groups include: (1) cleaning or exfoliating agents and (2) optionally conditioning agents.

The particulate cleansing or exfoliating agents can be derived from a wide variety of materials including those derived from inorganic, organic, natural, and synthetic sources.

The particulate cleansing or exfoliating agents of the present invention typically comprise from about 1% to about 5% alternatively from alternatively from about 0.5% to about 15% and alternatively from about 0.1% to about 30% by weight of the composition. Non-limiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polypropylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are particles made from mixed polymers (e.g., copolymers, terpolymers), among such are polyethylene/polypropylene copolymer, polyethylene/pro-pylene/isobutylene copolymer, polyethylene/styrene copolymer, and mixtures thereof. Typically, the polymeric and mixed polymeric particles are treated via an oxidation process to destroy impurities and the like. The polymeric and mixed polymeric particles can also optionally be cross linked with a variety of common crosslinking agents, non-limiting examples including butadiene, divinyl benzene, methylenebisacrylamide, allyl ethers of sucrose, allyl ethers of pentaerythritol, and mixtures thereof. Other examples of useful particles include waxes and resins such as paraffins, carnuba wax, ozekerite wax, candellila wax, urea-formaldehyde resins, and the like. When such waxes and resins are used herein it is important that these materials are solids at ambient and skin temperatures.

Water-insoluble, particulate materials useful herein are the synthetic polymeric particles and oils. Synthetic polymeric particles useful in the present invention are selected from the group consisting of polybutylene, polyethylene, polypropylene, polyisobutylene, polymethylstyrene, polypropylene, polystyrene, polyurethane, nylon, teflon, and mixtures thereof.

The conditioning particulate materials typically comprise from about 2% to 15%, alternatively from about 1% to about 20% alternatively from alternatively from about 0.5% to about 30% and alternatively from about 0.1% to about 50% by weight of the composition. These oils include but are not limited to hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin and its derivatives, wax esters, beeswax derivatives, sterols and phospholipids, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, poly alpha olefins, hydrogenated polyisobutenes and combinations thereof.

Non-limiting examples of silicone oils suitable for use herein include dimethicone copolyol, dimethylpolysiloxane, diethylpolysiloxane, mixed $C_1$-$C_{30}$ alkyl polysiloxanes, phenyl dimethicone, dimethiconol, and combinations thereof. Preferred are non-volatile silicones selected from dimethicone, dimethiconol, mixed $C_1$-$C_{30}$ alkyl polysiloxane, and combinations thereof. Non-limiting examples of silicone oils useful herein are described in U.S. Pat. No. 5,011,681.

Non-limiting examples of diglycerides and triglycerides suitable for use herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof. In addition any of the above oils that have been partially or fully hydrogenated are also suitable. Non-limiting examples of acetoglyceride esters suitable for use herein include acetylated monoglycerides.

Non-limiting examples of alkyl esters suitable for use herein include isopropyl esters of fatty acids and long chain esters of long chain fatty acids, e.g. SEFA (sucrose esters of fatty acids). Lauryl pyrolidone carboxylic acid, pentaerythritol esters, aromatic mono, di or triesters, and cetyl ricinoleate are non-limiting examples of which include isopropyl palmitate, isopropyl myristate, cetyl ricinoleate and stearyl ricinoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use herein include oleyl myristate, oleyl stearate, oleyl oleate, and combinations thereof. Non-limiting examples of lanolin and to lanolin derivatives suitable for use herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol ricinoleate, hydroxylated lanolin, hydrogenated lanolin and combinations thereof.

Suitable oils include milk triglycerides (e.g., hydroxylated milk glyceride) and polyol fatty acid polyesters. Suitable oils include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

The conditioning agents useful in the present invention are selected from the group consisting of droplets of emollient oils, skin care actives, vitamins, capsules and mixtures thereof. The capsules are generally made of gelatin, agar, or water-insoluble polymers and may contain emollient oils, vitamins, colored pigment, and additional ingredients, such as hair and skin actives as described below. Particle sizes of the capsules can range from about 5 to about 3000 microns.

5. Lathering Surfactants

The articles of the present invention also comprise one or more lathering surfactants. A lathering surfactant defined herein as surfactant, which when combined with water and mechanically agitated generates a foam or lather. Preferably, these surfactants or combinations of surfactants should be mild, which means that these surfactants provide sufficient cleansing or detersive benefits but do not overly dry the skin or hair while still lathering.

A wide variety of lathering surfactants are useful herein and include those selected from the group consisting of anionic lathering surfactants, nonionic lather surfactants, amphoteric lathering surfactants, and mixtures thereof. Generally, the lathering surfactants are fairly water soluble. When used in the composition, at least about 4% of the lathering surfactants have a HLB value greater than about ten. Examples of such surfactants are found in and U.S. Pat. No. 5,624,666, to Coffindaffer et al., issued Apr. 29, 1997. Cationic surfactants can also be used as optional components, provided they do not negatively impact the overall lathering characteristics of the required lathering surfactants Concentrations of these surfactant are from about 10% to about 20%, alternatively from about 6% to about 25%, and alternatively from about 4% to about 30% by weight of the composition. To avoid skin irritation issues, the compositions should have a ratio by weight of the composition of anionic surfactant to amphoteric and/or zwitterionic surfactant is from about 1.1:1 to about 1:1.5, alternatively from about 1.25:1 to about 1:2, and alternatively from about 1.5:1 to about 1:3.

Anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975 A wide variety of anionic lathering surfactants are useful herein. Non-limiting examples of anionic lathering surfactants include those selected from the group consisting of sarcosinates, sulfates, sulfonates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred. The alkoyl isethionates typically have the formula RCO—OCH$_2$CH$_2$SO$_3$M wherein R is alkyl or alkenyl, branched or linear of from about 10 to about 30 carbon atoms, preferably less than 20 carbon atoms, most preferably less than 18 carbon atoms and M is a water-soluble cation such as ammonium, sodium, potassium and triethanolamine. Non-limiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulas ROSO$_3$M and RO(C$_2$H$_4$O)$_x$SO$_3$M, wherein R is alkyl or alkenyl, branched or linear of from about 10 to about 30 carbon atoms, preferably less than 20 carbon atoms, most preferably less than 18 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R1\text{-}SO_3\text{-}M$$

wherein R1 is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates and pareth sulfonates having about 12 to about 24 carbon atoms, and b-alkyloxy alkane sulfonates.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853.

Other anionic materials include phosphates such as monoalkyl, dialkyl, and trialkylphosphate salts. Other anionic materials include alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and alkanolamine (e.g., triethanolamine), preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072, which is incorporated herein by reference in its entirety. Further non-limiting examples include ammonium, sodium, potassium and alkanolamine (e.g., triethanolamine) salts of lauroyl methyl taurate, myristoyl methyl taurate, and cocoyl methyl taurate. Also useful are lactylates, especially those having carbon chains between $C_8$ and $C_{16}$. Non-limiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between $C_8$ and $C_{16}$. Non-limiting examples of glutamates include ammonium, sodium, potassium and alkanolamine (e.g., triethanolamine) salts of lauroyl glutamate, myristoyl glutamate, and cocoyl glutamate.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Suitable amphoteric or zwitterionic detersive surfactants for use in the compositions herein include those which are known for use in hair care or other personal care cleansing. Concentration of such amphoteric detersive surfactants are from about 1% to about 10%, alternatively from about 0.5% to about 20% by weight of the composition. Non-limiting examples of suitable zwitterionic or amphoteric surfactants are described in U.S. Pat. No. 5,104,646 and U.S. Pat. No. 5,106,609.

Amphoteric detersive surfactants suitable for use in the compositions are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the present invention are selected from the group consisting of cocoamphoacetate, cocoamphodiacetate, lauroamphoacetate, lauroamphodiacetate, and mixtures thereof.

Commercially available amphoteric surfactants include those sold under the trade names Miranol C2M Conc. N.P., Miranol C2M Conc. O.P., Miranol C2M SF, Miranol CM Special, Miranol Ultra (Rhodia, Inc.); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercoteric MS-2 (Scher Chemicals).

Zwitterionic detersive surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Preferred zwitterionic detersive surfactants are the betaines and sulfobetaines, e.g., cocoamidopropylbetaine and cocoamidopropylhydroxysultaine.

Nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety. Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Alkyl glucosides and alkyl polyglucosides are useful herein, and can be broadly defined as condensation articles of long chain alcohols, e.g. $C_{8-30}$ alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$-$C_4$ alkyl, 2-hydroxyethyl, 2-hydroxypropyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polyhydroxy hydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060; U.S. Pat. No. 2,965,576; U.S. Pat. No. 2,703,798; and U.S. Pat. No. 1,985,424.

Other examples of nonionic surfactants include amine oxides. Amine oxides correspond to the general formula $R^1R^2R^3NO$, wherein $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

Non-limiting examples of preferred nonionic surfactants for use herein are those selected form the group consisting of $C_8$-$C_{18}$ glucose amides, $C_8$-$C_{18}$ alkyl polyglucosides, sucrose cocoate, sucrose laurate, lauramine oxide, cocoamine oxide, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, sodium myristoyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

6. Compositional pH

The personal cleansing composition of the present invention is preferably acidic, having a pH of less than about 7. In one embodiment the composition has a pH of less than about 5, or less than about 4. In one preferred embodiment the composition has a pH range of from about 2.5 to about 4.5

Suitable lathering surfactants for use at pH levels below about 4 can be selected from the group consisting of alkyl sulfonates, pareth sulfonates, sulfobetaines, alkylhydroxysultaines, alkylglucosides and mixtures thereof.

7. Additional Ingredients

The compositions of the present invention can contain a wide variety of ingredients including skin and hair care actives that are used in conventional product types, provided that they do not unacceptably alter the benefits of the invention. Additionally, these ingredients, when incorporated into the composition, should be suitable for use in contact with mammalian keratinous tissue without undue toxicity, incompatibility, instability, allergic response, and the like within the scope of sound judgment. The *International Cosmetic Ingredient Dictionary and Handbook*, 10<sup>th</sup> Edition (2004) describes a wide variety of non-limiting cosmetic and pharmaceutical ingredients commonly used in the skin care industry, which are suitable for use in the compositions of the present invention. Examples of these and similar ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., salicylic acid), anti-wrinkle agents, anti-inflammatory agents, anti-atrophy agents, anti-caking agents, desquamation agents, antimicrobial and antifungal agents (e.g., methylchloroisothiazolinone/methylisothiazolinone, iodopropynyl butylcarbamate), antioxidants, retinoids, N-acyl amino acid compounds, oil control agents (e.g., dehydroacetic acid or pharmaceutically acceptable salts) binders, biological additives, buffering agents, bulking agents, chelating agents, chemical additives, colorants, cosmetic astringents, cosmetic biocides, denaturants, drug astringents, emollients, external analgesics, film formers or materials, e.g., polymers, for aiding the film-forming properties or substantivity of the composition (e.g., copolymer of eicosene and vinyl pyrrolidone), humectants, opacifying agents, pH adjusters, propellants, reducing agents, sequestering agents, skin bleaching and lightening agents, skin-conditioning agents, skin firming agents, skin soothing and/or healing agents and derivatives, skin treating agents, surfactants, thickeners, amino sugars, and vitamins and derivatives thereof. Additional examples of suitable emulsifiers and surfactants can be found in, for example, U.S. Pat. No. 3,755,560, U.S. Pat. No. 4,421,769, and *McCutcheon's Detergents and Emulsifiers*, North American Edition, pages 317-324 (1986). It should be noted, however, that many materials may to provide more than one benefit, or operate via more than one mode of action. Therefore, classifications herein are made for the sake of convenience and are not intended to limit the active to that particular application or applications listed.

The personal cleansing composition can be used for many different purposes, including but not limited to use as a facial scrub or body scrub. This composition can be used in combination with other soaps or detergents as well as lotions or conditioners. Further, the present composition can be used with an exfoliating sponge or brush.

8. Composition Rheology—Yield Stress Test

Measurement of yield stress for these systems is conducted using a Brookfield YR-1 Yield Stress Rheometer (25° C., ~1 atm, RV spring, V72 vane spindle, secondary immersion point, 1.5 rpm, 5 min wait time) recorded after the sample is set for 3 days at 25 C under standard atmospheric pressure to allow for sufficient equilibration of colloidal structures. Those of skill in the art will understand that the yield stress can be measured on a sample having suspended particles or on samples without suspended particles. In one embodiment, the personal cleansing composition has a yield stress of about 2 Pa to about 50 Pa, or from about 5 Pa to about 40 Pa, or from about 10 Pa to about 30 Pa, or from about 15 to about 25 Pa, in accordance with the Yield Stress Test defined herein. The Yield Stress Test is defined at 25° C. Without intending to be bound by theory, it is believed that the yield stress can be correlated to particle suspension capabilities.

Without intending to be bound by theory, it is believed that yield stress is indicative of the ability of the personal cleansing composition to suspend particles. Where the yield stress of the personal cleansing composition is equal or greater than the stress applied by a single particle suspended, thus the particle, once suspended in the liquid matrix, should remain suspended and neither tend to float or sink. The stress applied by a suspended particle is determined based on the net force applied by the single bead, F, divided by the surface over which this force is applied, S.

$$\sigma_B = \frac{F}{S}$$

F depends on the difference in density between the liquid matrix and the suspension particle as well as the suspension particle volume.

$$F = \frac{4}{3} \cdot \pi \cdot R^3 \cdot (\rho_s - \rho_l) \cdot g$$

$\rho_s$ and $\rho_l$ are the densities of the suspended particle and the liquid matrix, respectively, and R is the radius of the bead, and g is gravity.

S, is calculated by:

$$S = K \cdot (4 \cdot \pi \cdot R^2)$$

K has been calculated to be a constant of 3.5.

In addition to this basic condition that the stress applied by one single bead or particle should not exceed the yield stress of the liquid matrix under static condition, the behavior of the system becomes more complicated when external stress are applied to the personal cleansing composition. Under the action of external forces such as during product pouring, the personal cleansing composition is forced to flow, thus the yield stress during the pouring process is reduced and after the pouring the microstructure require some time to restore the its at rest properties.

EXAMPLES

Samples of Examples 1-3 are made as follows. A bacterial cellulose network made of AxCel CG-PX (hereafter MFC) is activated by addition into deionized water and dispersion using high shear for at least 10 minutes. A separate premix of the secondary rheology modifying cationic polymer (1% w/w) is prepared in deionized water by mixing until dissolved. In examples which contain a nonionic polymer (secondary structurant) of Ceteareth-60 Myristyl Glycol (Elfacos GT-282S from AkzoNobel), such a cationic polymer premix is not prepared as above. Rather, the non-ionic polymer is melted in subsequent steps as a solid waxy component. Cationic polymer premix is added to the MFC premix. Hydrophilic conditioning agents, surfactants, hydrophilic powders, solid waxy components and salicylic acid are added sequentially thereafter. Gentle heat is applied to aid in melting of waxy components and dissolution of powders. Insoluble particulate materials and skin sensates are then added. The pH is adjusted to the desired target. If the pH is less than the desired target, then a pH control agent, typically a base such as sodium hydroxide, is added to raise the pH to the desired target. If the pH is greater than the desired target, then a pH control agent, typically an acid such as citric acid, is added to lower the pH to the desired target. Any additional ingredients, such as preservatives, fragrance, colorants/pigments, and the like, are then added upon cooling to room temperature.

TABLE 1

| Example | 1 | 2 | 3 |
|---|---|---|---|
| Water | QS to 100% (~60-70%) | QS to 100% (~60-70%) | QS to 100% (~60-70%) |
| Cocamidopropyl Hydroxysultaine[1] | 6.34% | 6.34% | 6.34% |
| Sodium C14-16 Olefin Sulfonate[2] | 4.00% | 4.00% | 4.00% |
| Sodium C12-15 Pareth-15 Sulfonate[3] | 1.30% | 1.30% | 1.30% |
| Glycerin | 2.00% | 2.00% | 2.00% |
| Sorbitol | 2.00% | 2.00% | 2.00% |
| Polypropylene[4] | 2.60% | 2.60% | 2.60% |
| Polyethylene, FD&C Blue 1 Lake[5] | 0.90% | 0.90% | 0.90% |
| AxCel CG-PX[6] | 0.25% | 0.25% | 0.25% |
| Salicylic Acid | 1.50% | 1.50% | 1.50% |
| Sodium Citrate | 0.10% | 0.10% | 0.10% |
| Miscellaneous Ingredients[7] | Up to 2% | Up to 2% | Up to 2% |
| Citric Acid | Add to pH 2.5-4.5 | Add to pH 2.5-4.5 | Add to pH 2.5-4.5 |
| Sodium Hydroxide | Add to pH 2.5-4.5 (~0.05%) | Add to pH 2.5-4.5 (~0.05%) | Add to pH 2.5-4.5 (~0.05%) |
| Secondary Rheology Modifying Polymer | | | |
| Polyquaternium-67[8] | | 0.10% | |
| Polyquaternium-10[9] | | | 0.10% |
| Stability - 3 months, 40° C. | Phase Separation | Stable | Stable |
| Yield Stress (Pa) | 15.77 | 33.24 | 18.78 |
| pH | 3.49 | 3.45 | 3.55 |

[1]MIRATAINE ® CBS from Rhodia Inc., Cranbury, NJ
[2]BIO-TERGE ® AS-40 CG-P from Stepan Co., Northfield, IL
[3]Avanel ® S 150 CG N from BASF, Ludwigshafen, Germany
[4]Propyltex 50PC from Micro Powders Inc., Tarrytown, NY
[5]Microblue 5025 from Micro Powders Inc., Tarrytown, NY
[6]Believed to be a 6:3:1 blend of Microfibrous cellulose, Xanthan Gum, Cellulose Gum according to US patent application 2008/0108714. From CP Kelco, San Diego, CA
[7]Miscellaneous ingredients include, but are not limited to perfume, skin sensates such as menthol or menthyl lactate, pigments, dyes, PEG-100, Disodium EDTA, other salts and other processing aids or viscosity modifying agents.
[8]SoftCAT ™ SL-5 from The Dow Chemical Co., Midland, Michigan
[9]UCARE ™ Polymer LR 400 from The Dow Chemical Co., Midland, Michigan Stability and Yield Stress Data Facial scrub formulas which exhibit bulk phase separation or stability under accelerated conditions (3 months at 40° C.) are shown in Table 1. Measurement of yield stress for the systems shown in Table 1 are conducted in accordance with the Yield Stress Test method defined herein. As shown in Table 1, a facial scrub formula containing only MFC (Example 1) as suspension polymer exhibited a yield stress of 15.77 pascals (Pa) yet is not completely stable, in that separation was observed where exfoliating particles began to float toward the surface. However, use of 0.1% polyquaternium-10 (LR400) with MFC (Example 3) increases the yield to stress by nearly 20% to 18.78 Pa and completely stabilizes the particles in the formula. Moreover, use of 0.1% polyquaternium-67 (SoftCAT SL-5) with MFC (Example 2) also results in a completely stable formula yet increased yield stress by over 110% to 33.24 Pa.

The personal care composition may exhibit a consumer preferred viscosity of greater than about 10,000 cps and less than about 50,000 cps. Viscosities are measured on a Brookfield DVII+Pro viscometer using a T-C bar spindle with a heliopath setting at 5 rpm at 25° C.

TABLE 2

Comparative Examples for Yield Stress Synergy Assessment

| Example | 4a* | 4b* | 5 | 6 | 7 |
|---|---|---|---|---|---|
| Water | QS to 100% | QS to 100% | QS to 100% | QS to 100% | QS to 100% |
| Cocamidopropyl Hydroxysultaine[10] | 6.34% | 6.34% | 6.34% | 6.34% | 6.34% |
| Sodium C14-16 Olefin Sulfonate[11] | 4.00% | 4.00% | 4.00% | 4.00% | 4.00% |
| Sodium C12-15 Pareth-15 Sulfonate[12] | 1.30% | 1.30% | 1.30% | 1.30% | 1.30% |
| Glycerin | 2.00% | 2.00% | 2.00% | 2.00% | 2.00% |
| Sorbitol | 2.00% | 2.00% | 2.00% | 2.00% | 2.00% |
| AxCel CG-PX[13] | 0.25% | 0.25% |  | 0.25% |  |
| Salicylic Acid | 1.50% | 1.50% | 1.50% | 1.50% | 1.50% |
| Sodium Citrate | 0.10% | 0.10% | 0.10% | 0.10% | 0.10% |
| Other Ingredients[14] | up to 2% | up to 2% | up to 2% | up to 2% | up to 2% |
| Citric Acid | Add to pH 2.5-4.5 | Add to pH 2.5-4.5 | Add to pH 2.5-4.5 | Add to pH 2.5-4.5 | Add to pH 2.5-4.5 |
| Sodium Hydroxide | Add to pH 2.5-4.5 (~0.05%) | Add to pH 2.5-4.5 (~0.05%) | Add to pH 2.5-4.5 (~0.05%) | Add to pH 2.5-4.5 (~0.05%) | Add to pH 2.5-4.5 (~0.05%) |
| Secondary Rheology Modifying Polymer |  |  |  |  |  |
| Polyquaternium-67[15] |  |  | 0.10% | 0.10% |  |
| Polyquaternium-10[16] |  |  |  |  | 0.10% |
| Polyquaternium-10[17] |  |  |  |  |  |
| Ceteareth-60 Myristyl Glycol[18] |  |  |  |  |  |
| Yield Stress (Pa) | 6.57 | 5.73 | 1.05 | 9.59 | Under range** |
| pH | 3.49 | 3.44 | 3.39 | 3.44 | 3.36 |

[10]MIRATAINE ® CBS from Rhodia Inc., Cranbury, NJ
[11]BIO-TERGE ® AS-40 CG-P from Stepan Co., Northfield, IL
[12]Avanel ® S 150 CG N from BASF, Ludwigshafen, Germany
[13]Believed to be a 6:3:1 blend of Microfibrous cellulose, Xanthan Gum, Cellulose Gum according to US patent application 2008/0108714. From CP Kelco, San Diego, CA
[14]Miscellaneous ingredients include, but are not limited to perfume, skin sensates such as menthol or menthyl lactate, pigments, dyes, PEG-100, Disodium EDTA, other salts and other processing aids or viscosity modifying agents.
*Examples 4a and 4b are the same formula prepared from different material lots where yield stresses were measured on separate days and under different environmental conditions as grouped in Simplified Example Sets 1 to 4.
**Under range (<1%) and Over range results are outside of the instrument detection limits for a given set of test parameters.

TABLE 3

Comparative Examples for Yield Stress Synergy Assessment

| Example | 8 | 9 | 10 | 11 | 12 |
|---|---|---|---|---|---|
| Water | QS to 100% | QS to 100% | QS to 100% | QS to 100% | QS to 100% |
| Cocamidopropyl Hydroxysultaine[19] | 6.34% | 6.34% | 6.34% | 6.34% | 6.34% |
| Sodium C14-16 Olefin Sulfonate[20] | 4.00% | 4.00% | 4.00% | 4.00% | 4.00% |
| Sodium C12-15 Pareth-15 Sulfonate[21] | 1.30% | 1.30% | 1.30% | 1.30% | 1.30% |
| Glycerin | 2.00% | 2.00% | 2.00% | 2.00% | 2.00% |
| Sorbitol | 2.00% | 2.00% | 2.00% | 2.00% | 2.00% |
| AxCel CG-PX[22] | 0.25% |  | 0.25% |  | 0.25% |
| Salicylic Acid | 1.50% | 1.50% | 1.50% | 1.50% | 1.50% |
| Sodium Citrate | 0.10% | 0.10% | 0.10% | 0.10% | 0.10% |
| Miscellaneous Ingredients[23] | Up to 2% | Up to 2% | Up to 2% | Up to 2% | Up to 2% |
| Citric Acid | Add to pH 2.5-4.5 | Add to pH 2.5-4.5 | Add to pH 2.5-4.5 | Add to pH 2.5-4.5 | Add to pH 2.5-4.5 |
| Sodium Hydroxide | Add to pH 2.5-4.5 (~0.05%) | Add to pH 2.5-4.5 (~0.05%) | Add to pH 2.5-4.5 (~0.05%) | Add to pH 2.5-4.5 (~0.05%) | Add to pH 2.5-4.5 (~0.05%) |

TABLE 3-continued

Comparative Examples for Yield Stress Synergy Assessment

| Example | 8 | 9 | 10 | 11 | 12 |
|---|---|---|---|---|---|
| Secondary Rheology Modifying Polymer | | | | | |
| Polyquaternium-67[24] | | | | | |
| Polyquaternium-10[25] | 0.10% | | | | |
| Polyquaternium-10[26] | | 0.10% | 0.10% | | |
| Ceteareth-60 | | | | 0.20% | 0.20% |
| Myristyl Glycol[27] | | | | | |
| Yield Stress (Pa) | 7.78 | Under range (<1 Pa)** | Over range (>10 Pa)** | 1.21 | 5.21 |
| pH | 3.38 | 3.35 | 3.34 | 3.37 | 3.40 |

[15]SoftCAT ™ SL-5 from The Dow Chemical Co., Midland, Michigan
[16]UCARE ™ Polymer LR 400 from The Dow Chemical Co., Midland, Michigan
[17]UCARE ™ Polymer LR 30M from The Dow Chemical Co., Midland, Michigan
[18]Elfacos ® GT-282S from AkzoNobel Surface Chemistry, Bridgewater, NJ
[19]MIRATAINE ® CBS from Rhodia Inc., Cranbury, NJ
[20]BIO-TERGE ® AS-40 CG-P from Stepan Co., Northfield, IL
[21]Avanel ® S 150 CG N from BASF, Ludwigshafen, Germany
[22]Believed to be a 6:3:1 blend of Microfibrous cellulose, Xanthan Gum, Cellulose Gum according to US patent application 2008/0108714. From CP Kelco, San Diego, CA
[23]Miscellaneous ingredients include, but are not limited to perfume, skin sensates such as menthol or menthyl lactate, pigments, dyes, PEG-100, Disodium EDTA, other salts and other processing aids or viscosity modifying agents.
[24]SoftCAT ™ SL-5 from The Dow Chemical Co., Midland, Michigan
[25]UCARE ™ Polymer LR 400 from The Dow Chemical Co., Midland, Michigan
[26]UCARE ™ Polymer LR 30M from The Dow Chemical Co., Midland, Michigan
[27]Elfacos ® GT-282S from AkzoNobel Surface Chemistry, Bridgewater, NJ
**Under range and Over range results are outside of the instrument detection limits for a given set of test parameters.

The addition of several secondary rheology modifiers with MFC imparts a synergistic increase in yield stress greater than the yield stress of MFC or polymeric rheology modifier alone (Tables 2 and 3). Examples 4-12 are prepared where exfoliating particles are excluded. Samples without sufficient structuring would rapidly phase separate, thus not allowing for accurate determination of the formula yield stress.

The samples from Tables 2 and 3 and Simplified Example Sets 1-4 have yield stress calculated as follows: Brookfield YR-1 Yield Stress Rheometer (25° C., ~1 atm, RV Spring, V71 spindle, secondary immersion mark, 2.5 rpm, 1 minute wait time) at least 3 days after making to allow for sufficient equilibration of colloidal structures. Notably, this test method is different from the test method defined in Section 8, herein, in order to calculate lower yield stress values than those which can be determined with the Yield Stress Test. As shown in Simplified Example Set 1, yield stresses of 6.57 and 1.05 Pa are observed for MFC and SL-5 alone, respectively. However, a synergy in yield stress through the combined use of the polymers is evident as the resulting yield stress was 9.59 Pa. This is 25% greater than the expected yield stress if the combination of polymers resulted in merely an additive increase. This synergy in yield stress results in a stable product when the product is formulated with exfoliating particles (e.g. Example 2). Synergies in yield stress are also observed using polyquaternium-10 as secondary rheology modifiers (Simplified Example Sets 2-3.) In comparison, Simplified Example set 4, including a known non-ionic associative thickener (Ceteareth-60 Myristyl Glycol Elfacos GT282S) was found not to be within the scope of the present invention.

As noted earlier Examples 4a and 4b are the same formula prepared from different material lots where yield stresses were measured on separate days and under different environmental conditions as grouped in Simplified Example Sets 1 to 4.

Simplified Example Set 1

| Example | 4a | 5 | 6 |
|---|---|---|---|
| Sample Description | 0.25% MFC, No SL-5 | No MFC, 0.1% SL-5 | 0.25% MFC, 0.1% SL-5 |
| Yield Stress (Pa) | 6.57 | 1.05 | 9.59 |
| % Synergistic Increase over Expected Additive Increase | | | 25.8% |

Simplified Example Set 2

| Example | 4a | 7 | 8 |
|---|---|---|---|
| Sample Description | 0.25% MFC, No LR400 | No MFC, 0.1% LR400 | 0.25% MFC, 0.1% LR400 |
| Yield Stress (Pa) | 6.57 | under range (<1 Pa) | 7.78 |
| % Synergistic Increase over Expected Additive Increase | | | at least 2.8% |

Simplified Example Set 3

| Example | 4b | 9 | 10 |
|---|---|---|---|
| Sample Description | 0.25% MFC, No LR30M | No MFC, 0.1% LR30M | 0.25% MFC, 0.1% LR30M |
| Yield Stress (Pa) | 5.73 | under range (<1 Pa) | Over range (>10 Pa) |
| % Synergistic Increase over Expected Additive Increase | | | at least 48.6% |

Simplified Example Set 4

| Example | 4b | 11 | 12 |
|---|---|---|---|
| Sample Description | 0.25% MFC, No GT282S | No MFC, 0.2% GT282S | 0.25% MFC, 0.2% GT282S |
| Yield Stress (Pa) | 5.73 | 1.21 | 5.21 |
| % Synergistic Increase over Expected Additive Increase | | | No Synergy |

Tables 4-6 provide additional examples of personal cleansing compositions within the scope of the present invention.

TABLE 4

Additional Examples

| Example | 13 | 14 | 15 | 16 | 17 |
|---|---|---|---|---|---|
| Water | QS to 100% (~60-70%) | QS to 100% (~60-70%) | QS to 100% (~60-70%) | QS to 100% (~60-70%) | QS to 100% (~60-70%) |
| Cocamidopropyl Hydroxysultaine[28] | 6.34% | 6.34% | 6.34% | 6.34% | 6.34% |
| Sodium C14-16 Olefin Sulfonate[29] | 4.00% | 4.00% | 4.00% | 4.00% | 4.00% |
| Sodium C12-15 Pareth-15 Sulfonate[30] | 1.30% | 1.30% | 1.30% | 1.30% | 1.30% |
| Glycerin | 2.00% | 2.00% | 2.00% | 2.00% | 2.00% |
| Sorbitol | 2.00% | 2.00% | 2.00% | 2.00% | 2.00% |
| Polypropylene[31] | 2.60% | | | | |
| Polyethylene[32] | | 1.75% | 1.75% | 1.75% | 4.00% |
| Polyethylene, FD&C Blue 1 Lake[33] | 0.90% | 1.00% | 1.00% | 1.00% | 1.25% |
| AxCel CG-PX[34] | 0.25% | 0.25% | 0.25% | 0.25% | 0.25% |
| Salicylic Acid | 1.50% | 1.50% | 1.50% | 1.50% | 1.50% |
| Sodium Citrate | 0.10% | 0.10% | 0.10% | 0.10% | 0.10% |
| Miscellaneous Ingredients[35] | Up to 2% | Up to 2% | Up to 2% | Up to 2% | Up to 2% |
| Menthol | | 0.09% | 0.09% | 0.09% | |
| Citric Acid | Add to pH 2.5-4.5 | Add to pH 2.5-4.5 | Add to pH 2.5-4.5 | Add to pH 2.5-4.5 | Add to pH 2.5-4.5 |
| Sodium Hydroxide | Add to pH 2.5-4.5 | Add to pH 2.5-4.5 | Add to pH 2.5-4.5 | Add to pH 2.5-4.5 | Add to pH 2.5-4.5 |
| Secondary Rheology Modifying Polymer | | | | | |
| Polyquaternium-67[36] | | 0.10% | 0.07% | 0.05% | 0.10% |
| Polyquaternium-10[37] | | | | | |
| Polyquaternium-10[38] | 0.10% | | | | |

[28]MIRATAINE ® CBS from Rhodia Inc., Cranbury, NJ
[29]BIO-TERGE ® AS-40 CG-P from Stepan Co., Northfield, IL
[30]Avanel ® S 150 CG N from BASF, Ludwigshafen, Germany
[31]Propyltex 50PC from Micro Powders Inc., Tarrytown, NY
[32]Microscrub 50PC from Micro Powders Inc., Tarrytown, NY
[33]Microblue 5025 from Micro Powders Inc., Tarrytown, NY
[34]Believed to be a 6:3:1 blend of Microfibrous cellulose, Xanthan Gum, Cellulose Gum according to US patent application 2008/0108714. From CP Kelco, San Diego, CA
[35]Miscellaneous ingredients include, but are not limited to perfume, skin sensates such as menthol or menthyl lactate, pigments, dyes, PEG-100, Disodium EDTA, other salts and other processing aids or viscosity modifying agents.

TABLE 5

Additional Examples

| Example | 18 | 19 | 20 | 21 | 22 |
|---|---|---|---|---|---|
| Water | QS to 100% (~60-70%) | QS to 100% (~60-70%) | QS to 100% (~60-70%) | QS to 100% (~60-70%) | QS to 100% (~60-70%) |
| Cocamidopropyl Hydroxysultaine[39] | 6.34% | 6.34% | 6.34% | 6.34% | 6.34% |
| Sodium C14-16 Olefin | 4.00% | 4.00% | 4.00% | 4.00% | 4.00% |

TABLE 5-continued

Additional Examples

| Example | 18 | 19 | 20 | 21 | 22 |
|---|---|---|---|---|---|
| Sulfonate[40] | | | | | |
| Sodium C12-15 Pareth-15 Sulfonate[41] | 1.30% | 1.30% | 1.30% | 1.30% | 1.30% |
| Glycerin | 2.00% | | | | |
| Sorbitol | 2.00% | | | | |
| Polypropylene[42] | | 2.60% | 2.60% | 2.60% | 2.60% |
| Polyethylene[43] | 4.00% | | | | |
| Polyethylene, FD&C Blue 1 Lake[44] | 1.25% | 0.90% | 0.90% | 0.90% | 0.90% |
| AxCel CG-PX[45] | 0.25% | 0.25% | 0.25% | 0.25% | 0.25% |
| Salicylic Acid | | 1.50% | 0.50% | | 1.50% |
| Sodium Citrate | 0.10% | 0.10% | 0.10% | 0.10% | 0.10% |
| Miscellaneous Ingredients[46] | Up to 2% | Up to 2% | Up to 2% | Up to 2% | Up to 2% |
| Menthol | 0.09% | | | | |
| Citric Acid | Add to pH 4.5-7.0 | Add to pH 2.5-4.5 | Add to pH 2.5-4.5 | Add to pH 4.5-7.0 | Add to pH 2.5-4.5 |
| Sodium Hydroxide | Add to pH 4.5-7.0 | Add to pH 2.5-4.5 | Add to pH 2.5-4.5 | Add to pH 4.5-7.0 | Add to pH 4.5-7.0 |
| Secondary Rheology Modifying Polymer | | | | | |
| Polyquaternium-67[47] | 0.10% | 0.10% | 0.10% | 0.10% | 0.10% |
| Polyquaternium-10[48] | | | | | |
| Polyquaternium-10[49] | | | | | |

[36]SoftCAT ™ SL-5 from The Dow Chemical Co., Midland, Michigan
[37]UCARE ™ Polymer LR 400 from The Dow Chemical Co., Midland, Michigan
[38]UCARE ™ Polymer LR 30M from The Dow Chemical Co., Midland, Michigan
[39]MIRATAINE ® CBS from Rhodia Inc., Cranbury, NJ
[40]BIO-TERGE ® AS-40 CG-P from Stepan Co., Northfield, IL
[41]Avanel ® S 150 CG N from BASF, Ludwigshafen, Germany
[42]Propyltex 50PC from Micro Powders Inc., Tarrytown, NY
[43]Microscrub 50PC from Micro Powders Inc., Tarrytown, NY
[44]Microblue 5025 from Micro Powders Inc., Tarrytown, NY
[45]Believed to be a 6:3:1 blend of Microfibrous cellulose, Xanthan Gum, Cellulose Gum according to US patent application 2008/0108714. From CP Kelco, San Diego, CA
[46]Miscellaneous ingredients include, but are not limited to perfume, skin sensates such as menthol or menthyl lactate, pigments, dyes, PEG-100, Disodium EDTA, other salts and other processing aids or viscosity modifying agents.

TABLE 6

Additional Examples (continued)

| Example | 23 | 24 | 25 | 26 | 27 |
|---|---|---|---|---|---|
| Water | QS to 100% (~60-70%) | QS to 100% (~50-60%) | QS to 100% (~50-60%) | QS to 100% (~50-60%) | QS to 100% (~50-60%) |
| Cocamidopropyl Hydroxysultaine[50] | 6.34% | 6.75% | 6.75% | 6.75% | 6.75% |
| Sodium C14-16 Olefin Sulfonate[51] | 4.00% | 5.28% | 5.28% | 5.28% | 5.28% |
| Sodium C12-15 Pareth-15 Sulfonate[52] | 1.30% | 2.25% | 2.25% | 2.25% | 2.25% |
| Glycerin | | 2.00% | 2.00% | | |
| Sorbitol | | 2.00% | 2.00% | | |
| Polypropylene[53] | 2.60% | 4.00% | 4.00% | 2.60% | 2.60% |
| Polyethylene[54] | | | | | |
| Polyethylene, FD&C Blue 1 Lake[55] | 0.90% | 1.25% | 1.25% | 0.90% | 0.90% |
| AxCel CG-PX[56] | 0.25% | 0.25% | 0.25% | 0.25% | 0.25% |
| Salicylic Acid | 0.50% | 1.50% | | 2.00% | |
| Sodium Citrate | 0.10% | 0.10% | 0.10% | 0.10% | 0.10% |
| Miscellaneous Ingredients[57] | Up to 2% | Up to 2% | Up to 2% | Up to 2% | Up to 2% |
| Menthol | | 0.09% | 0.09% | 0.09% | 0.09% |
| Citric Acid | Add to pH 2.5-4.5 | Add to pH 2.5-4.5 | Add to pH 4.5-7.0 | Add to pH 2.5-4.5 | Add to pH 4.5-7.0 |
| Sodium Hydroxide | Add to pH 2.5-4.5 | Add to pH 2.5-4.5 | Add to pH 4.5-7.0 | Add to pH 2.5-4.5 | Add to pH 4.5-7.0 |

TABLE 6-continued

Additional Examples (continued)

| Example | 23 | 24 | 25 | 26 | 27 |
|---|---|---|---|---|---|
| Secondary Rheology Modifying Polymer | | | | | |
| Polyquaternium-6[58] | | 0.05% | 0.05% | 0.07% | 0.07% |
| Polyquaternium-10[59] | 0.10% | | | | |
| Polyquaternium-10[60] | | | | | |

[47]SoftCAT ™ SL-5 from The Dow Chemical Co., Midland, Michigan
[48]UCARE ™ Polymer LR 400 from The Dow Chemical Co., Midland, Michigan
[49]UCARE ™ Polymer LR 30M from The Dow Chemical Co., Midland, Michigan
[50]MIRATAINE ® CBS from Rhodia Inc., Cranbury, NJ
[51]BIO-TERGE ® AS-40 CG-P from Stepan Co., Northfield, IL
[52]Avanel ® S 150 CG N from BASF, Ludwigshafen, Germany
[53]Propyltex 50PC from Micro Powders Inc., Tarrytown, NY
[54]Microscrub 50PC from Micro Powders Inc., Tarrytown, NY
[55]Microblue 5025 from Micro Powders Inc., Tarrytown, NY
[56]Believed to be a 6:3:1 blend of Microfibrous cellulose, Xanthan Gum, Cellulose Gum according to US patent application 2008/0108714. From CP Kelco, San Diego, CA
[57]Miscellaneous ingredients include, but are not limited to perfume, skin sensates such as menthol or menthyl lactate, pigments, dyes, PEG-100, Disodium EDTA, other salts and other processing aids or viscosity modifying agents.
[58]SoftCAT ™ SL-5 from The Dow Chemical Co., Midland, Michigan
[59]UCARE ™ Polymer LR 400 from The Dow Chemical Co., Midland, Michigan
[60]UCARE ™ Polymer LR 30M from The Dow Chemical Co., Midland, Michigan All percentages disclosed herein, unless otherwise stated, are by weight of the named material itself that is found in the compositions, thereby excluding for example the weight associated with carriers, impurities and by-products found in the raw material.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern.

Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid composition comprising:
   a. from about 0.05% to about 0.5% of a bacterial cellulose network;
   b. from about 0.005% to about 0.5% of a cationic polymer which is hydrophobically modified with a hydrophobic substituent and a cationic substituent;
   c. from about 0.1% to about 30% of a particulate material;
   d. from about 4% to about 30% of a lathering surfactant comprising an anionic surfactant selected from the group consisting of sarcosinates, sulfates, sulfonates, isethionates, taurates, phosphates, lactylates, glutamates, and mixtures thereof;
   e. a compositional pH of less than about 4; and wherein the liquid composition has a yield stress of about 2 Pa to about 50 Pa in accordance with the Yield Stress Test defined herein.

2. The composition of claim 1, wherein the hydrophobically modified cationic polysaccharide comprises a cellulose ether which has from 4,000 to 10,000 anhydroglucose repeat units.

3. The composition of claim 2, wherein the hydrophobically modified cationic polysaccharide is substituted with:
   (a) on the average from 0.0003 to 0.08 moles, per mole of anhydroglucose unit, of a substituent comprising an alkyl or arylalkyl group having from 8 to 24 carbon atoms and
   (b) a substituent having the formula

[R5R6R7R8N+]($A^{z-}$)$_{1/z}$ wherein R5, R6 and R7 each independently are —CH3 or —C2H5, R8 is —CH2—CHOH—CH2— or —CH2CH2—, Az- is an anion, and z is 1, 2 or 3.

4. The composition of claim 3, wherein said hydrophobically modified cationic polysaccharide comprises a cellulose ether selected from the group consisting of: hydroxyethyl cellulose, hydroxypropyl cellulose, methyl cellulose, hydroxypropyl methyl cellulose, hydroxyethyl methyl cellulose, hydroxyethyl carboxymethyl cellulose, or mixtures thereof.

5. The composition of claim 1, wherein the bacterial cellulose network comprises a widest cross sectional microfiber width of from about 1.6 nm to about 200 nm.

6. The composition of claim 1, wherein the bacterial cellulose network comprises an length to cross sectional width aspect ratio of about 10:1 to about 1000:1.

7. The composition of claim 1, comprising from about 0.01% to about 0.5% of said cationic polymer.

8. The composition of claim 1, further comprising a second cationic polymer selected from the group consisting of a derivatized quaternized hydroxyethyl cellulose ether, a cationic polysaccharide polymers, a cellulose ether, a guar gum, and a mixture thereof.

9. The composition of claim 1, wherein the cationic polymer comprises a cationic polysaccharide polymer has the formula:

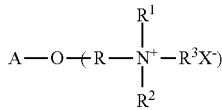

wherein A is an anhydroglucose residual group; R is selected from an alkylene oxyalkylene, polyoxyalkylene, hydroxyalkylene group, and a combination thereof;

R1, R2, and R3 are independently selected from alkyl, aryl, alkylaryl, arylalkyl, alkoxyalkyl, alkoxyaryl groups and combinations thereof, each group containing up to about 18 carbon atoms, and the total number of carbon atoms in R1, R2 and R3 being less than about 20; and X is an anionic counterion.

10. The composition of claim 9, wherein the cationic polysaccharide polymers has the formula:

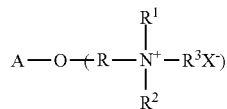

wherein A is an anhydroglucose residual group; R is selected from an alkylene oxyalkylene, polyoxyalkylene, hydroxyalkylene group, and a combination thereof;

R1, R2, and R3 are independently selected from alkyl, aryl, alkylaryl, arylalkyl, alkoxyalkyl, alkoxyaryl groups and combinations thereof, each group containing up to about 18 carbon atoms, and the total number of carbon atoms in R1, R2 and R3 being less than about 20; and X is an anionic counterion.

11. The composition of claim 1, wherein the particulate materials are selected from the group consisting of cleaning agents, exfoliating agents, skin conditioning agents and mixtures thereof derived from inorganic, organic, natural, and synthetic sources.

12. The composition of claim 11, wherein said particulate material has a largest lateral dimension of from about 5 to about 3000 microns.

13. The composition of claim 1, wherein the lathering surfactant further comprises an additional surfactant selected from the group consisting of nonionic lather surfactants, amphoteric lathering surfactants, and zwitterionic lathering surfactants and mixtures thereof.

14. The composition of claim 13, wherein the lathering surfactant is at a level wherein the Average Lather Volume of the composition is greater than or equal to about 15 ml.

* * * * *